United States Patent
Enami (10) Patent No.: US 10,863,997 B2
(45) Date of Patent: Dec. 15, 2020

(54) MEDICAL DEVICE

(71) Applicant: ASAHI INTECC CO., LTD., Seto (JP)

(72) Inventor: Yukiko Enami, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 318 days.

(21) Appl. No.: 15/394,152

(22) Filed: Dec. 29, 2016

(65) Prior Publication Data

US 2017/0273697 A1 Sep. 28, 2017

(30) Foreign Application Priority Data

Mar. 25, 2016 (JP) .................................. 2016-062405

(51) Int. Cl.
*A61B 17/22* (2006.01)
*A61B 17/3207* (2006.01)
(Continued)

(52) U.S. Cl.
CPC ...... *A61B 17/22* (2013.01); *A61B 17/320725* (2013.01); *A61M 29/02* (2013.01);
(Continued)

(58) Field of Classification Search
CPC ............ A61B 17/22; A61B 17/320725; A61B 17/3205; A61B 2017/22051; A61B 2017/320716; A61B 2017/22011; A61B 2017/22034; A61B 2017/22037; A61B 2017/22081; A61B 2017/22001; A61B 2017/22072; A61B 2017/2212;
(Continued)

(56) References Cited

U.S. PATENT DOCUMENTS

| 5,490,859 A | 2/1996 | Mische et al. |
| 5,501,694 A | 3/1996 | Ressemann et al. |

(Continued)

FOREIGN PATENT DOCUMENTS

| EP | 0 719 111 B1 | 1/2001 |
| EP | 0 794 734 B1 | 8/2002 |

(Continued)

OTHER PUBLICATIONS

Jul. 27, 2017 Extended European Search Report issued in European Patent Application No. 16203576.0.

(Continued)

*Primary Examiner* — Katherine H Schwiker
(74) *Attorney, Agent, or Firm* — Oliff PLC (57) ABSTRACT

A medical device includes a mesh member capable of radially expanding and contracting, and a cylindrical member located at one end of the mesh member. The mesh member is woven from a first wire and a second wire. The cylindrical member includes a wrapping portion and a lining portion that are fixed to each other at fixation portions positioned within spaces defined by the first wire and the second wire. Neither the wrapping portion nor the lining portion is fixed to either of the first wire or the second wire. Upon expansion or radial contraction of the mesh member, movement of the first wire or the second wire is not interfered with by the cylindrical member. This reduces the concentration of stress at the end of the mesh member and thus the likelihood that either the first wire or the second wire will break.

20 Claims, 10 Drawing Sheets (51) Int. Cl.
*A61M 29/02* (2006.01)
*A61M 25/10* (2013.01)

(52) U.S. Cl.
CPC ............... *A61M 2025/109* (2013.01); *A61M 2025/1081* (2013.01)

(58) Field of Classification Search
CPC .. A61B 2017/2215; A61M 2025/1084; A61M 29/02; A61M 2025/109; A61M 2025/1081; A61M 2025/1086; A61M 2025/1088; A61M 25/104; A61M 2025/1075; A61F 2002/072; A61F 2002/075; A61F 2002/077; A61F 2002/9511; A61F 2002/9505; A61F 2/07; A61F 2/90; A61F 2/91; A61F 2/915; A61F 2/86; A61F 2/01; A61F 2/013; A61F 2/02; A61F 2002/91508; A61F 2002/91516; A61F 2002/91525; A61F 2002/91533; A61F 2002/91541; A61F 2002/9155; A61F 2002/91558; A61F 2002/91566; A61F 2002/91575; A61F 2002/91583; A61F 2002/91591; A61F 2002/011; A61F 2002/015; A61F 2002/016; A61F 2002/018

See application file for complete search history.

(56) References Cited

U.S. PATENT DOCUMENTS

| | | | |
|---|---|---|---|
| 5,540,707 | A | 7/1996 | Ressemann et al. |
| 5,769,887 | A * | 6/1998 | Brown ............ A61F 2/07 |
| | | | 606/194 |
| 5,792,157 | A | 8/1998 | Mische et al. |
| 5,836,868 | A | 11/1998 | Ressemann et al. |
| 5,897,567 | A | 4/1999 | Ressemann et al. |
| 6,858,034 | B1 * | 2/2005 | Hijlkema ........... A61F 2/95 |
| | | | 606/108 |
| 8,992,553 | B2 | 3/2015 | Diamant et al. |
| 2002/0058985 | A1 * | 5/2002 | DePalma .......... A61F 2/07 |
| | | | 623/1.13 |
| 2004/0176832 | A1 * | 9/2004 | Hartley ............. A61F 2/07 |
| | | | 623/1.11 |
| 2005/0033311 | A1 * | 2/2005 | Guldfeldt ........ A61M 25/0074 |
| | | | 606/108 |
| 2005/0149161 | A1 | 7/2005 | Eidenschink et al. |
| 2005/0222667 | A1 * | 10/2005 | Hunt ............... A61F 2/07 |
| | | | 623/1.13 |
| 2006/0036311 | A1 * | 2/2006 | Nakayama ......... A61F 2/90 |
| | | | 623/1.15 |
| 2006/0052865 | A1 * | 3/2006 | Banas .............. A61F 2/07 |
| | | | 623/1.44 |
| 2006/0229714 | A1 | 10/2006 | Lombardi et al. |
| 2007/0185457 | A1 * | 8/2007 | Euteneuer ....... A61B 17/22032 |
| | | | 604/170.02 |
| 2010/0087907 | A1 * | 4/2010 | Lattouf .......... A61B 17/12022 |
| | | | 623/1.11 |
| 2012/0239064 | A1 * | 9/2012 | Cartier ............ A61B 17/221 |
| | | | 606/159 |
| 2015/0127087 | A1 * | 5/2015 | Kim ................ A61F 2/07 |
| | | | 623/1.13 |

FOREIGN PATENT DOCUMENTS

| | | |
|---|---|---|
| JP | 2002-536056 A | 10/2002 |
| JP | 3566288 B2 | 9/2004 |
| JP | 2007-516770 A | 6/2007 |
| JP | 2015-173913 A | 10/2015 |
| JP | 2015173913 A * | 10/2015 |
| WO | 98/50101 A1 | 11/1998 |
| WO | 00/45742 A1 | 8/2000 |
| WO | 2005/067818 A1 | 7/2005 |
| WO | 2014/063039 A1 | 4/2014 |

OTHER PUBLICATIONS

Jul. 23, 2019 Office Action issued in Japanese Patent Application No. 2016-062405.

* cited by examiner

MEDICAL DEVICE

CROSS REFERENCE TO RELATED APPLICATION

This application claims priority to Japanese Application No. 2016-062405 filed on Mar. 25, 2016, the contents of which are incorporated by reference herein in their entirety.

BACKGROUND

The disclosed embodiments relate to a medical device comprising a mesh member capable of expanding and contracting (expandable and contractible) radially.

Conventionally, a stenosis or stricture formed in a blood vessel or in a digestive organ is treated by a well-known method (PTCA: percutaneous transluminal coronary angioplasty), in which the stenosis or stricture is dilated with a medical device such as a balloon catheter. Such a medical device generally has an expandable-and-contractible member capable of radially expanding and radially contracting (e.g., a balloon or a mesh member), and the expandable-and-contractible member radially expands to dilate the stenosis or stricture.

When the stenosis or stricture is highly calcified, however, it is difficult to dilate it with a balloon-type expandable-and-contractible member. So, for a calcified stenosis or stricture, a medical device comprising a mesh-type expandable-and-contractible member is often used (see Japanese Patent Application Publication No. 2015-173913 (JP 2015-173913 A) discussed below, for example).

The medical device (an angioplasty catheter) of JP 2015-173913 A comprises a mesh member made from a scoring element. A lining portion (a ring-shaped member) covers an inner circumference of an end of the mesh member, and a wrapping portion (a covering tube) covers an outer circumference of the end of the mesh member.

In this medical device, the lining portion (the ring-shaped member) and the wrapping portion (the covering tube) are firmly and securely fixed to the end of the mesh member. Because of this firm fixation, upon radial expansion or radial contraction of the mesh member, the lining portion (the ring-shaped member) and the wrapping portion (the covering tube) interfere with the movement of the wires that constitute the mesh member, which is a problem. Specifically, they interfere with changes in the angles made by the wires with respect to the longitudinal axis of the mesh member. As a consequence, high stress is concentrated at the end of the mesh member, and the wires that constitute the mesh member are likely to break, which is also a problem. Especially when the mesh member is made to expand in a stenosis or stricture that is calcified and formed in a curved section of a blood vessel or a digestive organ, the mesh member cannot properly follow the curved contour of the blood vessel or the digestive organ and the mesh member fails to dilate at the stenosis or stricture, or the wires that constitute the mesh member break.

SUMMARY

The disclosed embodiments have been devised based on the above circumstances, and an object of the disclosed embodiments is to provide a medical device in which movement of wires that constitute a mesh member of the medical device is not likely to be interfered with, concentration of stress at an end of the mesh member upon radial expansion or radial contraction of the mesh member is reduced, and consequently the wires that constitute the mesh member are not likely to break.

This object may achieved in the following ways.

A medical device of the disclosed embodiments comprises a mesh member capable of radially expanding and radially contracting, the mesh member being woven from a first wire and a second wire; and a cylindrical member comprising a wrapping portion and a lining portion. The wrapping portion covers an outer circumference of at least one end of the mesh member, and the lining portion covers an inner circumference of the at least one end of the mesh member. The wrapping portion and the lining portion are fixed to each other at fixation portions, which are within spaces defined by the first wire and the second wire. Neither the wrapping portion nor the lining portion is fixed to either of the first wire or the second wire.

Because of this configuration, upon radial expansion or radial contraction of the mesh member, movement of the first wire and the second wire is not likely to be interfered with by the cylindrical member, and consequently the concentration of stress at the end of the mesh member is reduced. The likelihood that the first wire or the second wire that constitute the mesh member will break is therefore reduced. In addition, because this configuration gives the first wire and the second wire a certain degree of freedom in their movement, the mesh member, when made to expand in a stenosis or stricture that is formed in a curved section of a blood vessel or a digestive organ, can follow the curved contour of the blood vessel or the digestive organ and can dilate the stenosis or stricture more reliably than a conventional device.

An outer surface of the wrapping portion of the cylindrical member may be composed of depressed sections and projected sections (i.e., may be a "projected-and-depressed outer surface"), with the depressed sections being formed at the fixation portions, and the projected sections being formed where the wrapping portion and the lining portion are not fixed to each other. This configuration provides a reduced area of contact between the wrapping portion of the cylindrical member and the wall of the blood vessel or the wall of the digestive organ, reducing frictional resistance upon insertion of the medical device into the blood vessel or the digestive organ. This configuration therefore facilitates delivery of the medical device to the site of the stenosis or stricture, and is preferable particularly for a stenosis or stricture formed in a sharply curved peripheral vessel because the wrapping portion of the cylindrical member is less likely to be caught on the wall of the blood vessel or the wall of the digestive organ.

Additionally, the lining portion may include a space, and the wrapping portion may include a space. That is, the lining portion and the wrapping portion are not continuous in the circumferential direction. In this configuration, the wrapping portion and the lining portion are fixed to each other at fixation portions located at each space. The lining portion can thus be formed by fixing ends of a rolled tabular member to the wrapping portion, and the wrapping portion can be formed by fixing ends of a rolled tabular member to the lining portion.

When the cylindrical member is located at the proximal end of the mesh member, the medical device may further comprise a shaft fixed to the projected-and-depressed outer surface of the wrapping portion and extending beyond the cylindrical member toward a proximal end of the medical device. The shaft is fixed to the cylindrical member at the depressed sections of the projected-and-depressed outer surface that are formed at the fixation portions. The shaft provides an anchoring effect that can enhance the fixation between the shaft and the cylindrical member, reducing the possibility of the shaft coming off the cylindrical member.

The medical device may further comprise a second cylindrical member on the other end of the mesh member. The second cylindrical member comprises a second wrapping portion and a second lining portion, the second wrapping portion and a second lining portion being fixed to each other at second fixation portions, and the second fixation portions being within spaces that are defined by the first wire and the second wire. Neither the second wrapping portion nor the second lining portion is fixed to either of the first wire or the second wire. Because of this configuration, upon expansion or contraction of the mesh member, movement of the first wire and the second wire is not likely to be interfered with, and consequently the concentration of stress at either end of the mesh member is reduced so that the likelihood of breakage of the first wire or the second wire that constitute the mesh member is further reduced.

DETAILED DESCRIPTION OF EMBODIMENTS

Figure 1:
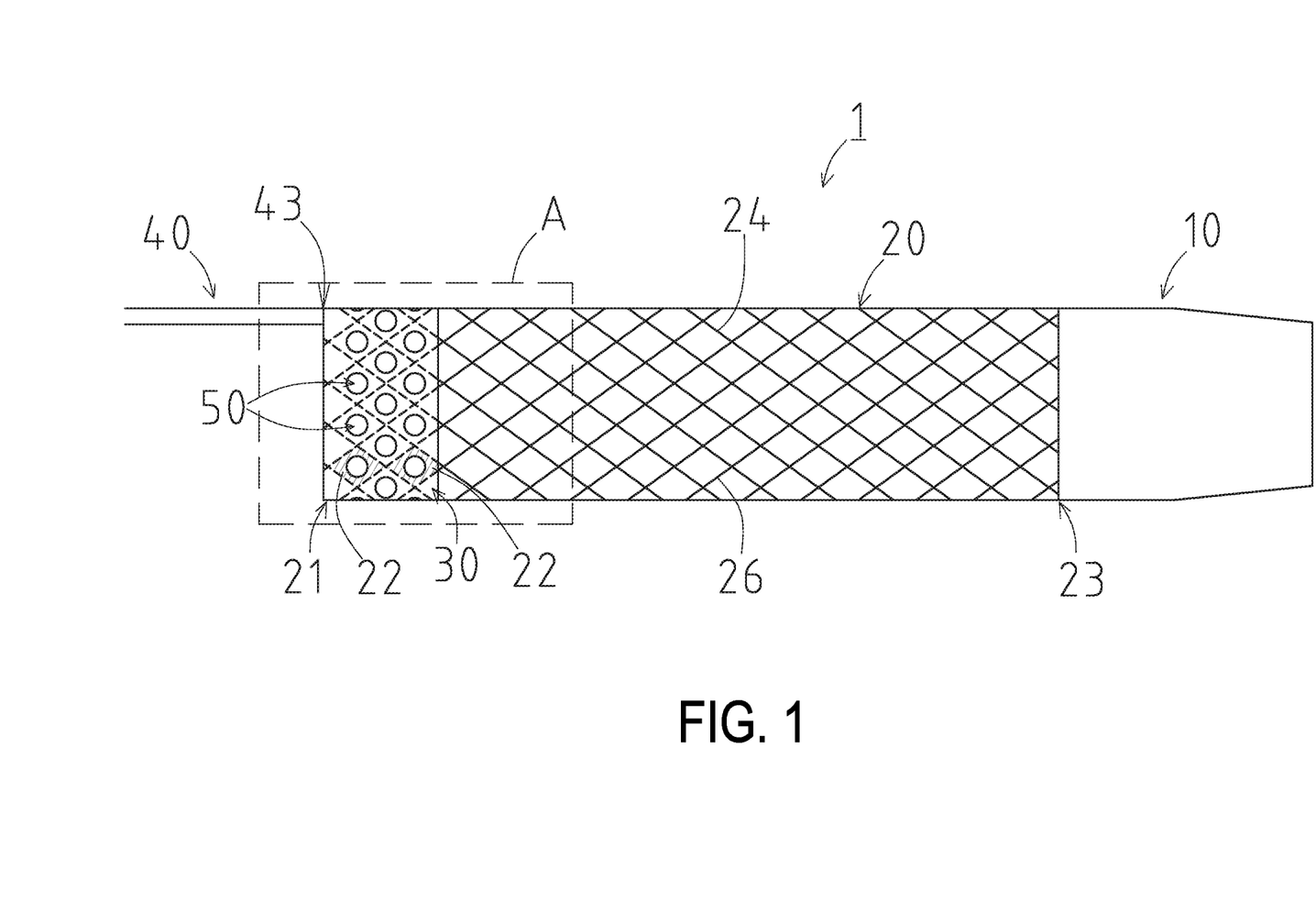
FIG. 1 is an overall view of a medical device according the disclosed embodiments, in which the mesh member is radially contracted.
Figure 2:
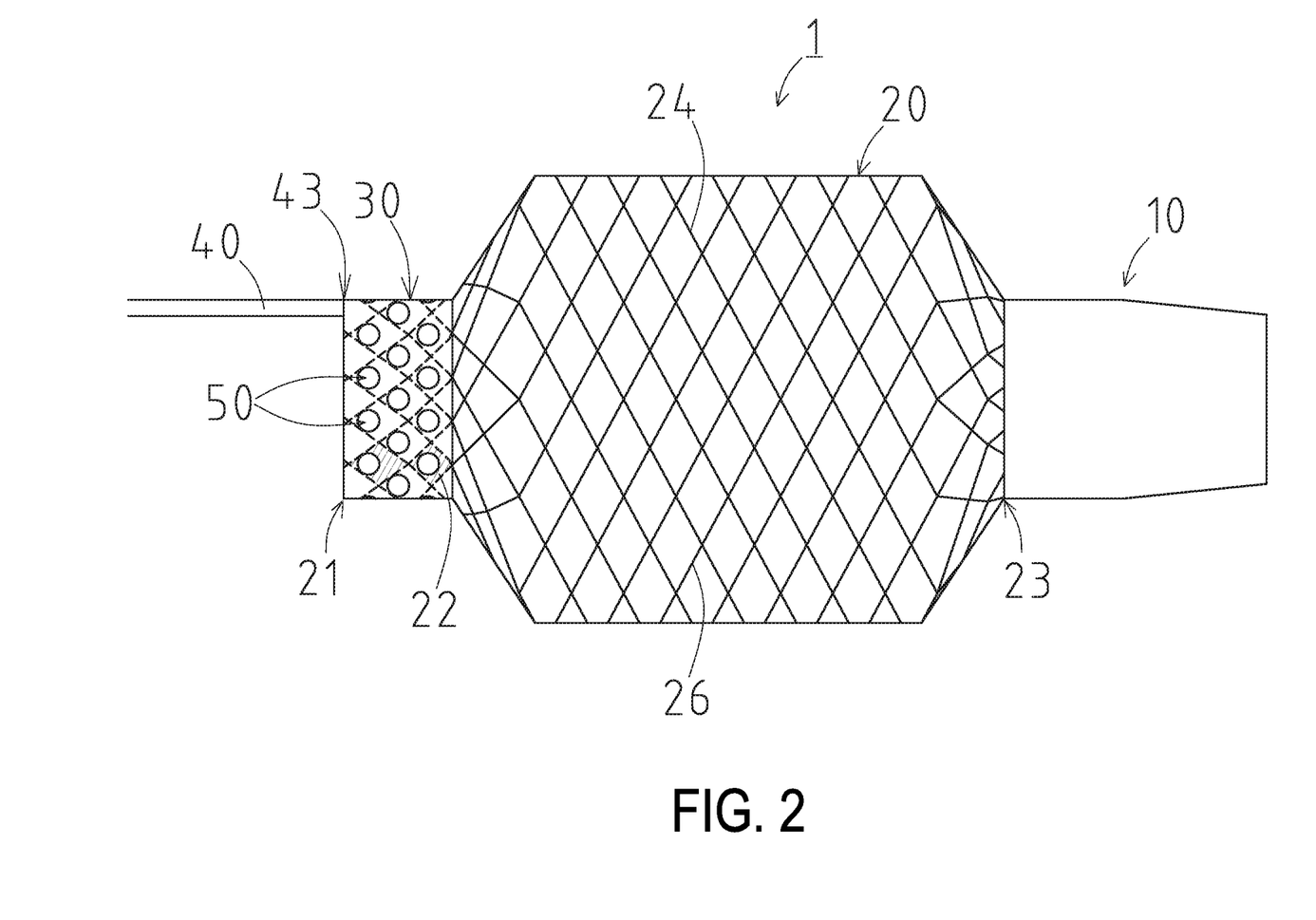
FIG. 2 is an overall view of the medical device shown in FIG. 1, in which the mesh member is radially expanded.

A medical device 1 according to the disclosed embodiments is described below with reference to FIG. 1 to FIG. 5. In FIG. 1 to FIG. 4, the right side corresponds to the distal end (the front end) to be inserted into the body, and the left side corresponds to the proximal end (base end) to be manipulated by a handler such as a doctor. FIG. 1 shows a mesh member 20 radially contracted, and FIG. 2 shows the mesh member 20 radially expanded.

The medical device 1 is, for example, a therapeutic device used for dilating a stenosis or stricture for curative purposes. As shown in FIG. 1 and FIG. 2, the medical device 1 comprises a distal tip 10, a mesh member 20 capable of radially expanding and radially contracting, a cylindrical member 30, and a shaft 40.

The mesh member 20 has a mesh configuration (a net configuration) woven from at least a first wire 24 and a second wire 26. The first wire 24 and the second wire 26 may be made of a Co—Cr alloy with high tensile strength, but the material is not limited thereto. For example, the first wire 24 and the second wire 26 may be made of a metal material such as stainless steel, W, Pt, a Pt—Ni alloy, a Ni—Ti alloy, or a Cu—Al—Ni alloy; or a resin material such as polyester, polyurethane, polyolefin, polytetrafluoroethylene, or a silicone resin. The material of the first wire 24 may be different from the material of the second wire 26.

Preferably, at least one of the first wire 24 and the second wire 26 is made of a radiopaque material (tungsten, for example) because the handler can use imaging to see exactly where the mesh member 20 is and to easily place the mesh member 20 in a stenosis or stricture.

The distal tip 10 is fixed to a distal end 23 of the mesh member 20. The distal tip 10 may be formed of a resin, such as polyurethane.

Figure 4:
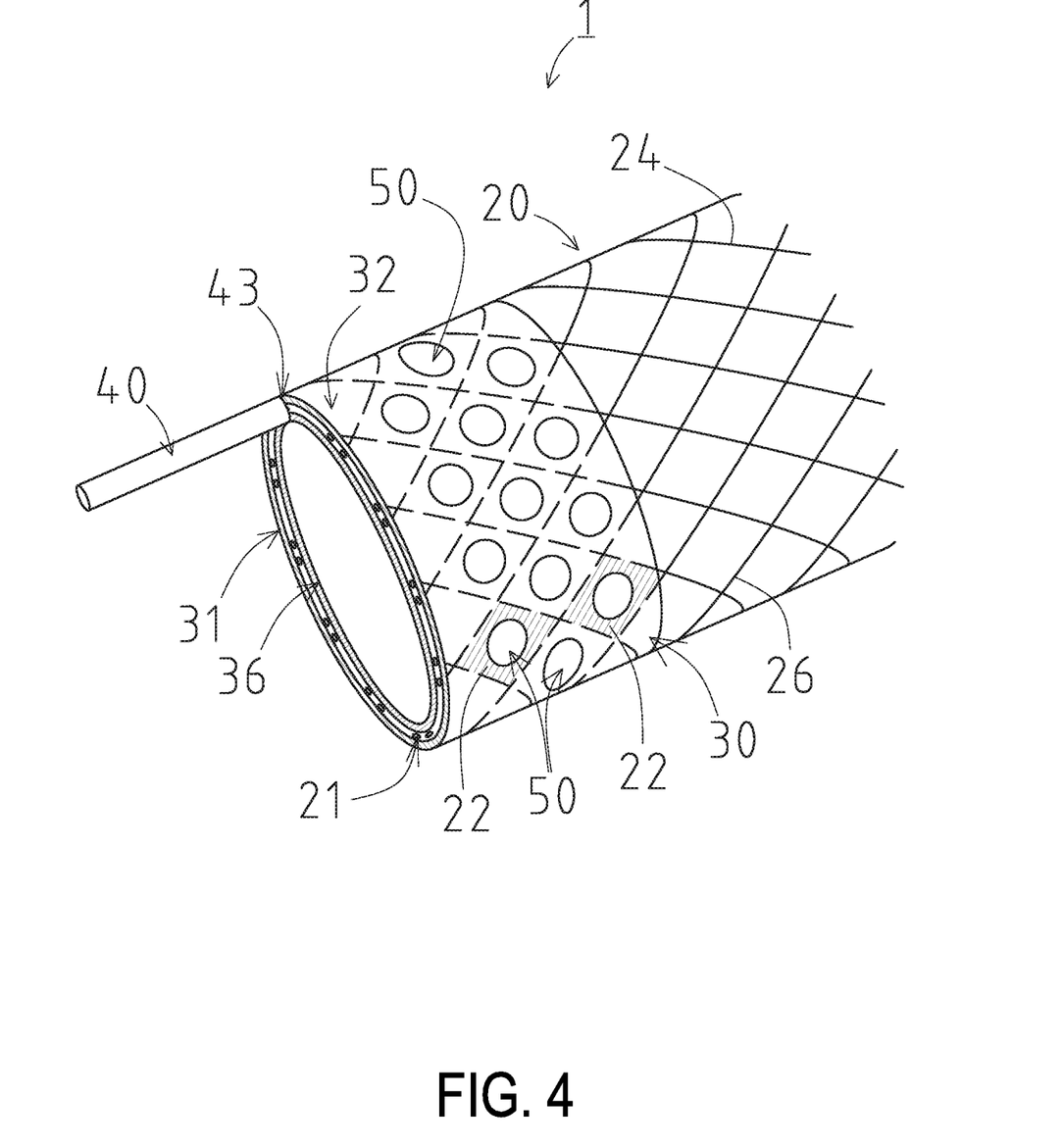
FIG. 4 is a perspective view of the part of the medical device shown in FIG. 3.
Figure 5:
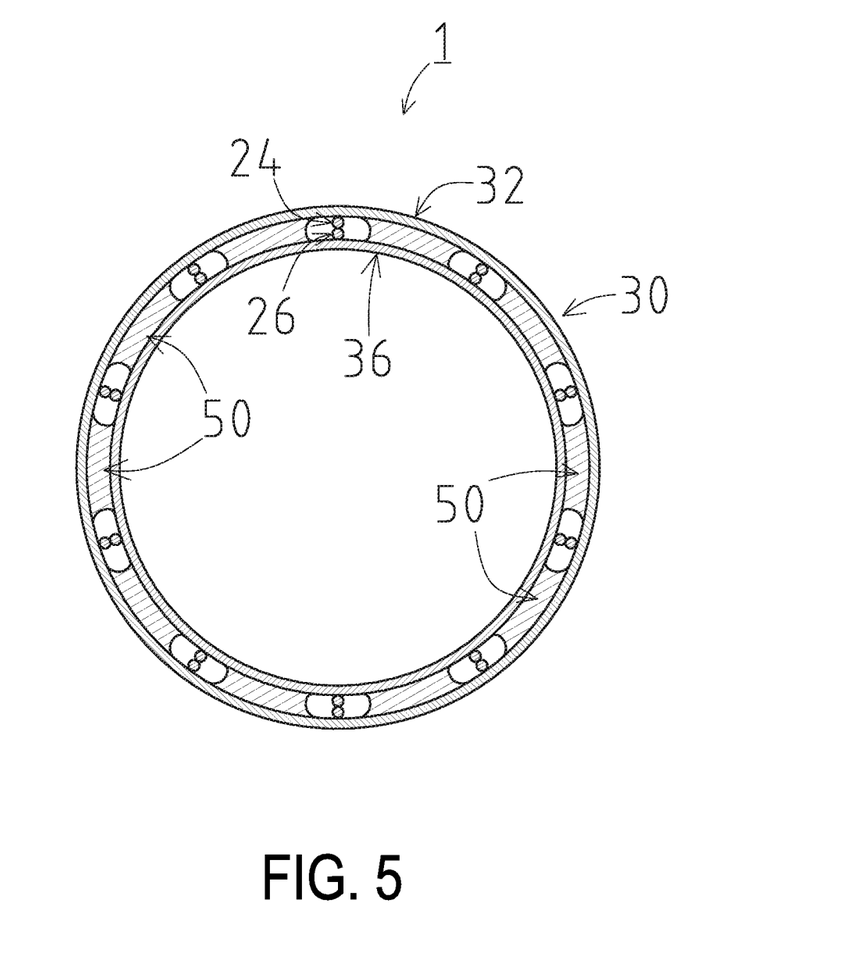
FIG. 5 is a sectional view taken from line D-D of FIG. 3.

The cylindrical member 30 is fixed to a proximal end 21 of the mesh member 20. As shown in FIG. 4 and FIG. 5, the cylindrical member 30 has a wrapping portion 32 covering an outer circumference of the proximal end 21 of the mesh member 20, as well as a lining portion 36 covering an inner circumference of the proximal end 21 of the mesh member 20. Therefore, the outer circumference and the inner circumference of the proximal end 21 of the mesh member 20 are covered with the wrapping portion 32 and the lining portion 36 of the cylindrical member 30.

Figure 3:
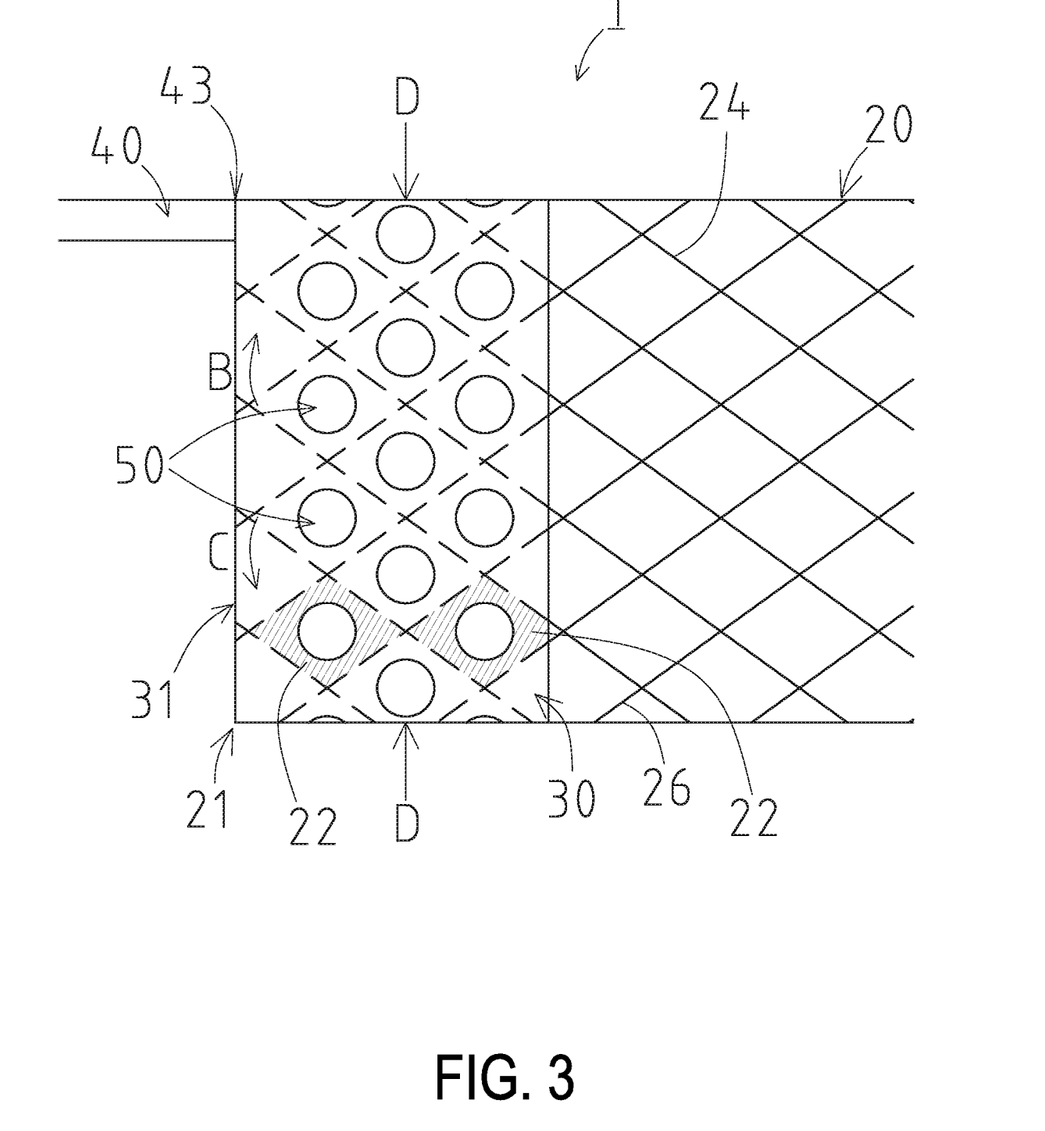
FIG. 3 is an expanded view of part A in FIG. 1.

As shown in FIG. 3 and FIG. 4, a distal end 43 of the shaft 40 is fixed to a proximal end 31 of the cylindrical member 30. The shaft 40 is a thin, cylinder-like metal wire (e.g., a stainless steel wire), extending from the proximal end 31 of the cylindrical member 30 in the longitudinal direction of the medical device toward the proximal end of the medical device.

The handler inserts the medical device 1 into a blood vessel or a digestive organ and manipulates the shaft 40 in the longitudinal direction to deliver the medical device 1 to the site of a stenosis or stricture. During this procedure, the mesh member 20 is radially contracted (see FIG. 1). Subsequently, the handler inserts a balloon catheter (not shown) into the interior of the mesh member 20 of the medical device 1 and then radially expands the balloon of the balloon catheter so as to radially expand the mesh member 20 (see FIG. 2). By pressing the mesh member 20 against the stenosis or stricture, the handler can dilate the stenosis or stricture.

In FIG. 2, the balloon catheter inserted in the interior of the mesh member 20 is omitted for ease of understanding. The balloon catheter used in the medical device 1 can be a known balloon catheter.

In the medical device 1, the wrapping portion 32 and the lining portion 36 are fixed to each other at fixation portions 50, with the fixation portions 50 being within spaces 22 on the circumference of the cylindrical member 30 that are defined by the first wire 24 and the second wire 26. Neither the wrapping portion 32 nor the lining portion 36 is fixed to either of the first wire 24 or the second wire 26 that constitute the mesh member 20 (see FIG. 4 and FIG. 5). The wrapping portion 32 and the lining portion 36 of the cylindrical member 30 may be made of stainless steel and fixed to each other within the spaces 22 with an adhesive. However, the method of providing the fixation portions 50 is not particularly limited.

Because of this configuration, upon radial expansion (in other words, upon transitioning from the state shown in FIG. 1 to the state shown in FIG. 2) or radial contraction (in other words, upon transitioning from the state shown in FIG. 2 to the state shown in FIG. 1) of the mesh member 20, movement of the first wire 24 or the second wire 26 is not likely to be interfered with by the cylindrical member 30, and consequently the concentration of stress at the proximal end 21 of the mesh member 20 is reduced. The likelihood of breakage of the first wire 24 or the second wire 26 that constitute the mesh member 20 is therefore reduced. As shown in FIG. 3, upon expansion of the mesh member 20, the first wire 24 can move toward the direction B and the second wire 26 can move toward the direction C. As described here, because the first wire 24 and the second wire 26 are not fixed to the cylindrical member 30, the first wire 24 and the second wire 26 can move with a certain degree of freedom. As a result, the mesh member 20, when made to expand in a stenosis or stricture that is formed in a curved section of a blood vessel or a digestive organ, can follow the curved contour of the blood vessel or the digestive organ and can dilate the stenosis or stricture more reliably than a conventional device.

The degree of freedom in the movement of the first wire 24 and the second wire 26 can be controlled, as appropriate, by changing the size, shape, and/or number of the fixation portions 50 within the spaces 22.

Figure 6:
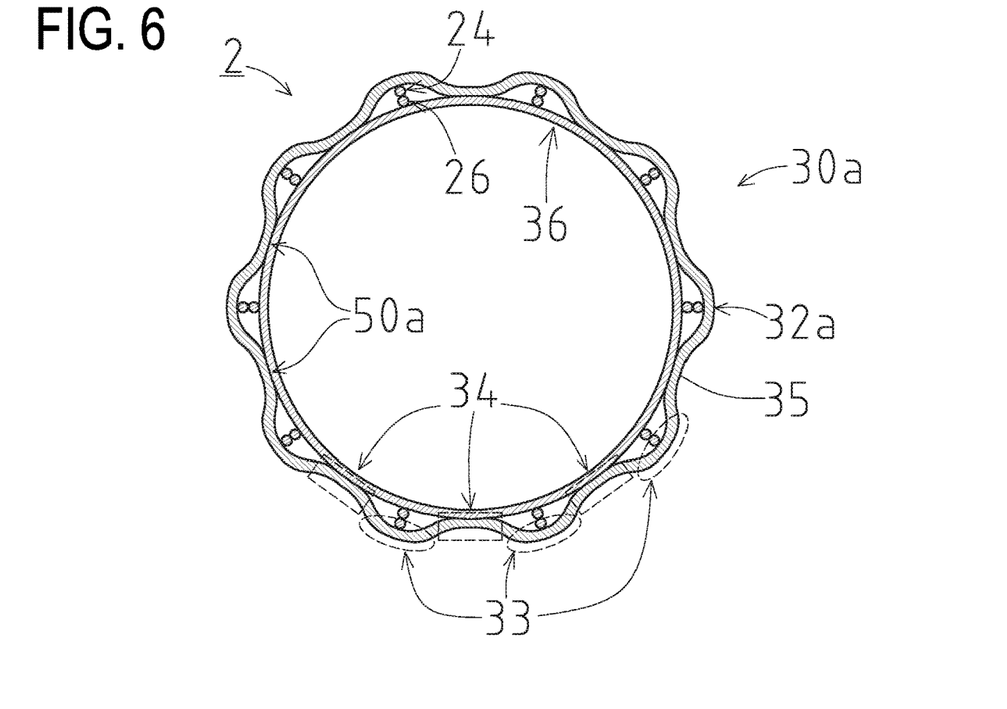
FIG. 6 shows part of a medical device according to the disclosed embodiments.

A medical device 2 according to the disclosed embodiments is described below with reference to FIG. 6. The following descriptions with respect to FIG. 6 to FIG. 11 only reflect differences from the medical device 1. In the medical device 2, a wrapping portion 32a of a cylindrical member 30a has a projected-and-depressed outer surface 35. More specifically, the projected-and-depressed outer surface 35 of the wrapping portion 32a is composed of depressed sections 34 and projected sections 33. The depressed sections 34 are formed within the spaces 22 at fixation portions 50a at which the wrapping portion 32a and the lining portion 36 are fixed to each other. The projected sections 33 are formed where the wrapping portion 32a and the lining portion 36 are not fixed to each other.

This configuration provides a reduced area of contact between the wrapping portion 32a of the cylindrical member 30a and the wall of the blood vessel or the wall of the digestive organ, reducing frictional resistance upon insertion of the medical device 2 into the blood vessel or the digestive organ. This configuration therefore allows easy delivery of the medical device 2 to the site of the stenosis or stricture, and is preferable particularly for a stenosis or stricture formed in a sharply curved peripheral vessel, because the wrapping portion 32a of the cylindrical member 30a is less likely to be caught on the wall of the blood vessel or the wall of the digestive organ.

The method of forming the fixation portions 50a is not particularly limited. For example, the wrapping portion 32a with the projected-and-depressed outer surface 35 may be prepared in advance, followed by the formation of the fixation portions 50a by adhering the wrapping portion 32a and the lining portion 36 to each other using an adhesive. Alternatively, a laser may be applied from outside to the spaces 22 in the cylindrical member 30 of the medical device 1. By this laser application, the fixation portions 50a at which the wrapping portion 32a and the lining portion 36 are fixed to each other are formed, and, at the same time, the projected-and-depressed outer surface 35 of the wrapping portion 32a is formed.

Figure 7:
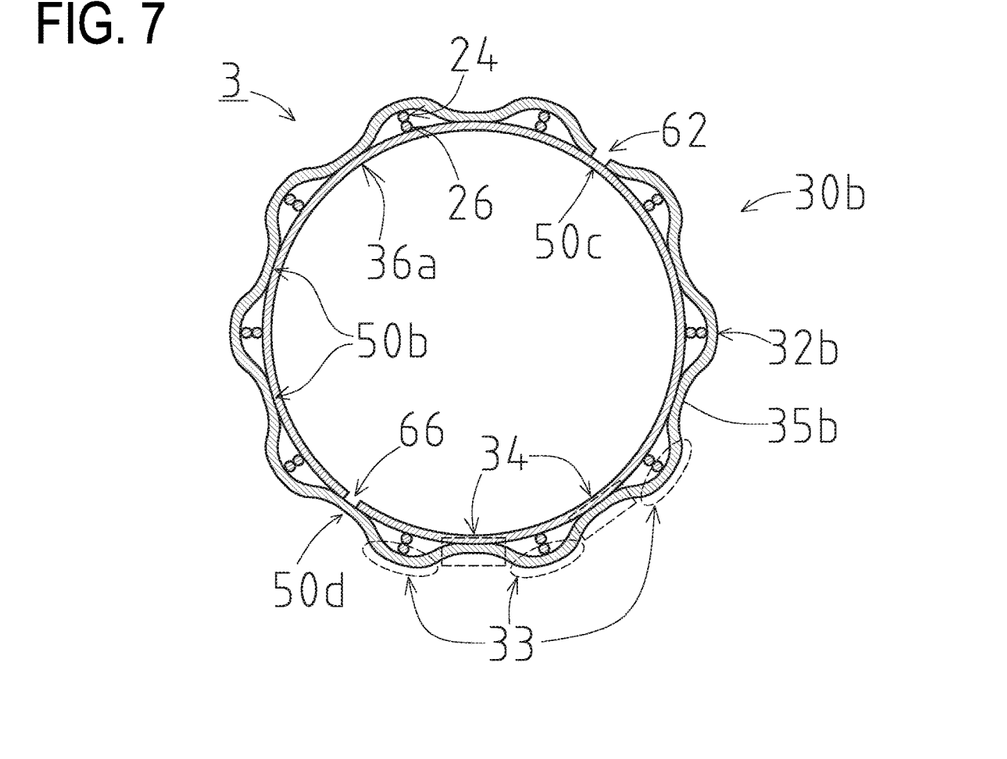
FIG. 7 shows part of a medical device according to the disclosed embodiments.

Next, a medical device 3 according to the disclosed embodiments is described below with reference to FIG. 7. In the medical device 3, similar to the wrapping portion 32a of the medical device 2, a wrapping portion 32b of a cylindrical member 30b has a projected-and-depressed outer surface 35b composed of the depressed sections 34 and the projected sections 33, and it also has a space 62. In addition, a lining portion 36a of the cylindrical member 30b has a space 66. At the space 62, the wrapping portion 32b and the lining portion 36a are fixed to each other at a fixation portion 50c, and at the space 66, the wrapping portion 32b and the lining portion 36a are fixed to each other at a fixation portion 50d. The wrapping portion 32b and the lining portion 36a are also fixed to each other at the depressed portions 34 at fixation points 50b.

In the configuration of the cylindrical member 30b of the medical device 3, the lining portion 36a (which is a rolled stainless steel tabular member covering the inner circumference of the proximal end 21 of the mesh member 20) is fixed to the wrapping portion 32b (which is a rolled stainless steel tabular member covering the outer circumference of the proximal end 21 of the mesh member 20) at the fixation portions 50b, 50c, and 50d. In FIG. 7, the two ends of the tabular member that are to be made into the lining portion 36a are spaced from each other in order to form the space 66 in the lining portion 36a, while the two ends of the tabular member that are to be made into the wrapping portion 32b are spaced from each other in order to form the space 62 in the wrapping portion 32b. Due to this configuration of the cylindrical member 30b, there is no need to provide the cylindrical lining portion 36 or the cylindrical wrapping portion 32 or 32a as required in the cylindrical member 30 or 30a, but instead, the wrapping portion 32b can be formed into a cylindrical shape by fixing the ends of the tabular member for forming the wrapping portion 32b to the lining portion 36a at the fixation portion 50c. In the same manner, the lining portion 36a can be formed into a cylindrical shape by fixing the ends of the tabular member for forming the lining portion 36a to the wrapping portion 32b at the fixation portion 50d.

Figure 8:
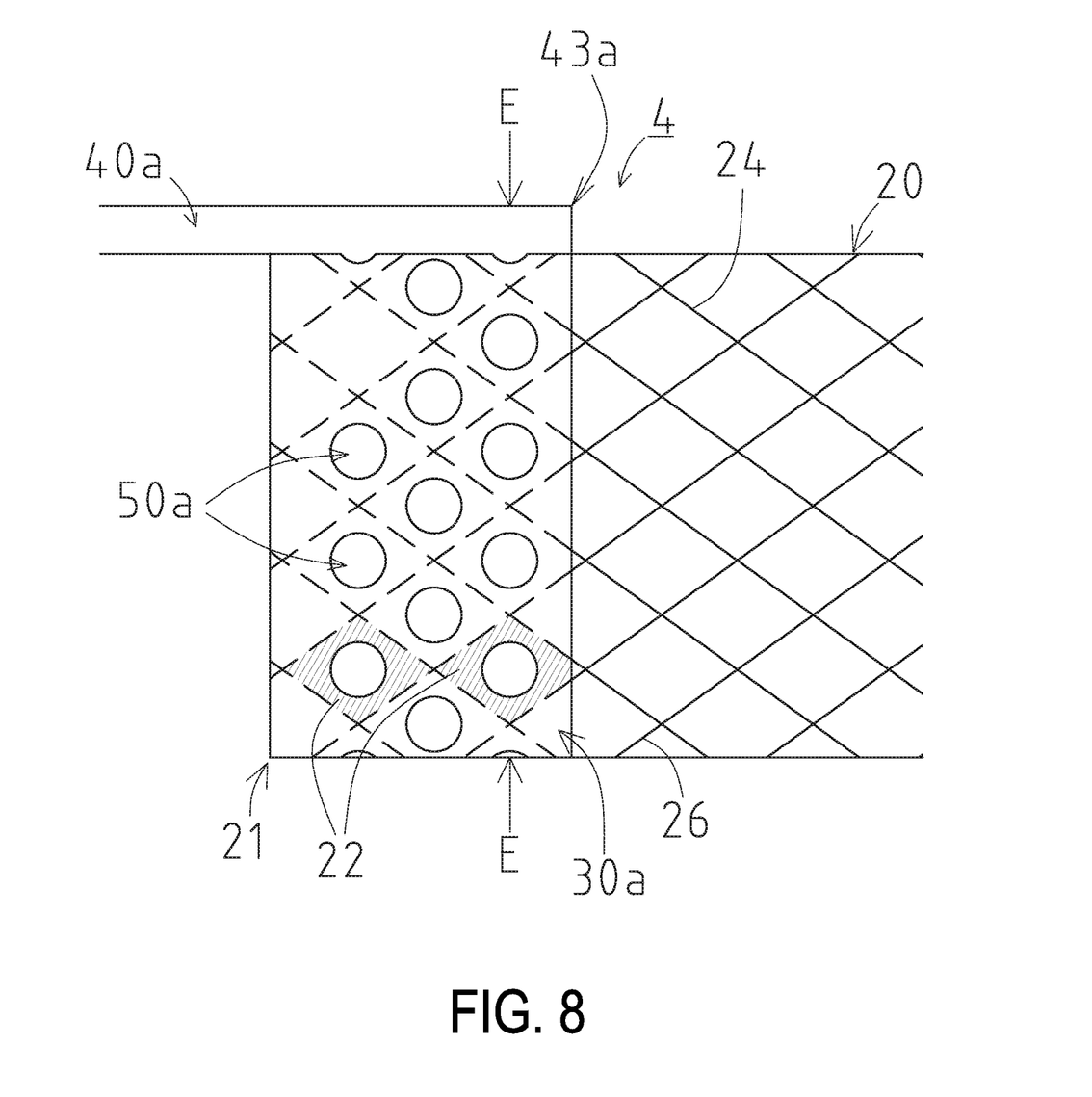
FIG. 8 shows part of a medical device according to the disclosed embodiments.
Figure 9:
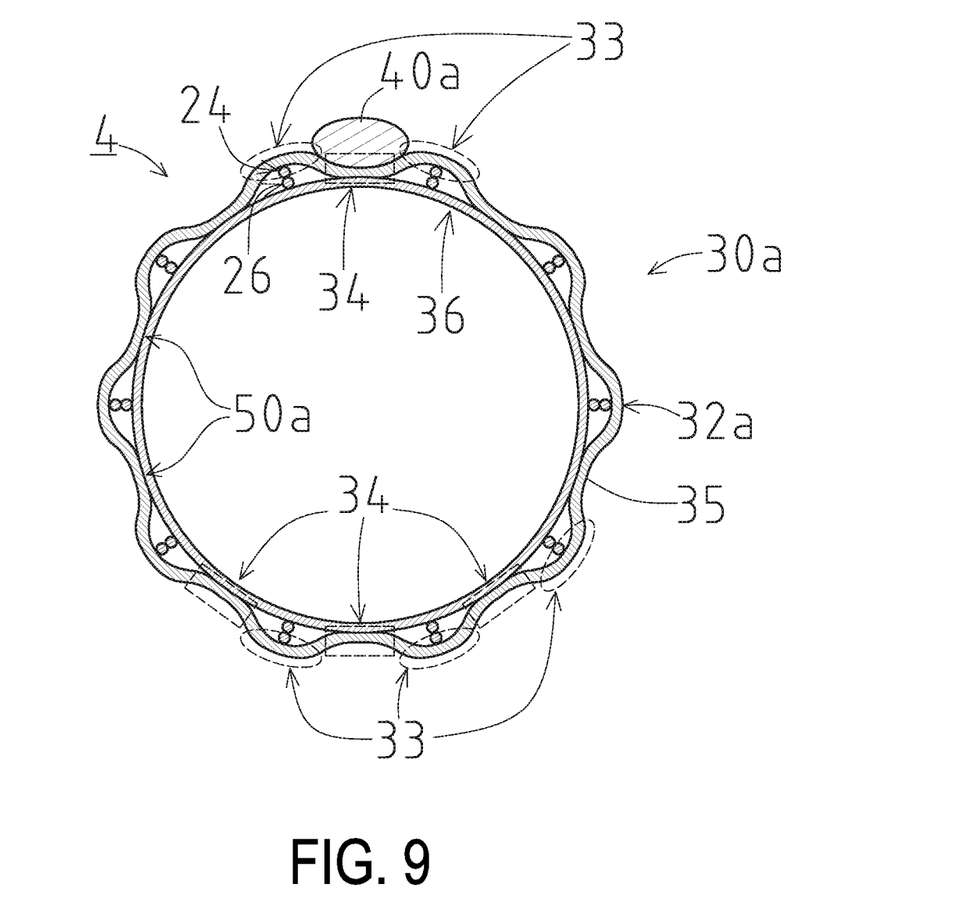
FIG. 9 is a sectional view taken from line E-E of FIG. 8.

Next, a medical device 4 according to the disclosed embodiments is described below reference to FIG. 8 and FIG. 9. As shown in FIG. 8 and FIG. 9, the distal end 43a of the shaft 40a of the medical device 4 extends to the distal end of the cylindrical member 30a and is fixed to the outer surface 35 of the wrapping portion 32a of the cylindrical member 30a. The shaft 40a extends in the longitudinal direction and covers some of the fixation portions 50a at which the wrapping portion 32a and the lining portion 36 of the cylindrical member 30a are fixed to each other. As shown in FIG. 9, the shaft 40a is fixed to the cylindrical member 30a at least in part at the depressed sections 34 of the wrapping portion 32a.

Because the shaft 40a is thus buried at least in part at the fixation portions 50a in the depressed sections 34 of the wrapping portion 32a, the shaft 40a provides an anchoring effect that enhances the fixation between the shaft 40a and the cylindrical member 30a, reducing the possibility of the shaft 40a coming off of the cylindrical member 30a.

As shown in FIG. 9, the cross-sectional profile of the shaft 40a may be elliptical so that it can fit into the depressed sections 34 of the outer surface 35 of the wrapping portion 32a of the cylindrical member 30a. This shape can increase the contact area at which the shaft 40a and the cylindrical member 30a are fixed to each other, and, as a result, can further enhance the fixation between the shaft 40a and the cylindrical member 30a.

Figure 10:
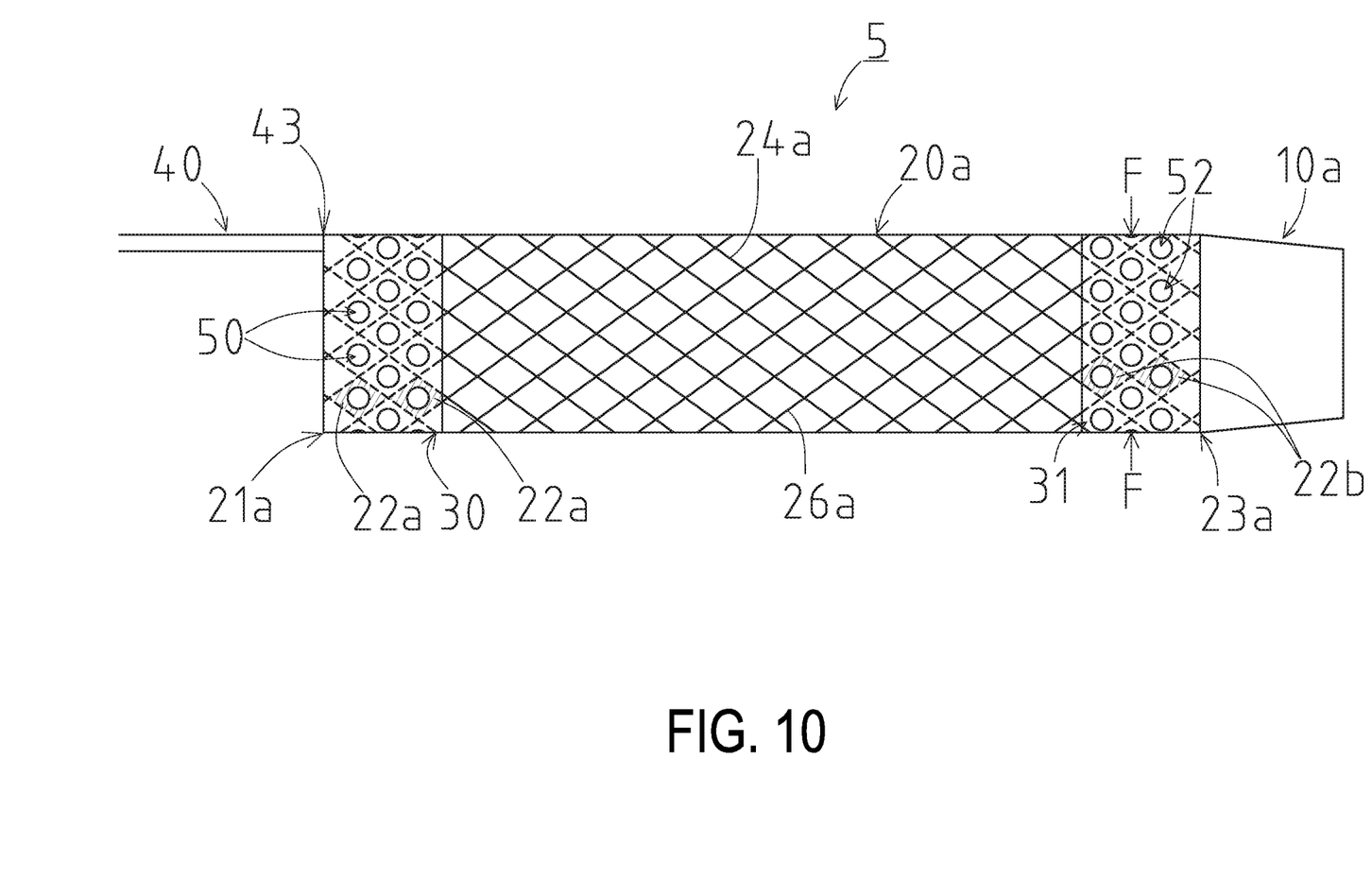
FIG. 10 is an overall view of a medical device according to the disclosed embodiments.
Figure 11:
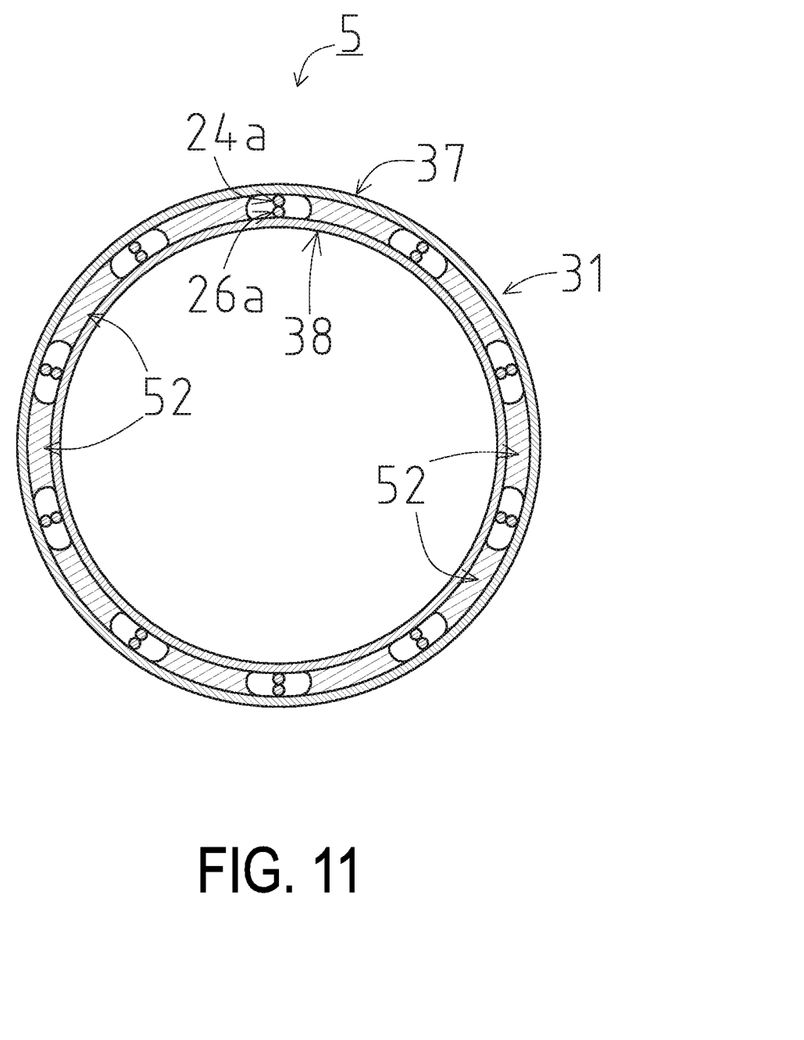
FIG. 11 is a sectional view taken from line F-F of FIG. 10.

Lastly, a medical device 5 according to the disclosed embodiments is described below with reference to FIG. 10 and FIG. 11. As shown in FIG. 10, a mesh member 20a is attached at a proximal end 21a to the cylindrical member 30 (a first cylindrical member), and is attached at a distal end 23a to a second cylindrical member 31. As shown in FIG. 11, similarly to the cylindrical member 30, the second cylindrical member 31 has a second wrapping portion 37 covering an outer circumference of the distal end 23a of the mesh member 20a as well as a second lining portion 38 covering an inner circumference of the distal end 23a of the mesh member 20a. Therefore, the outer circumference and the inner circumference of the proximal end 21a of the mesh member 20a are covered with the wrapping portion 32 and the lining portion 36 of the cylindrical member 30, and the outer circumference and the inner circumference of the distal end 23a of the mesh member 20a are covered with the second wrapping portion 37 and the second lining portion 38 of the second cylindrical member 31.

The distal end of the second cylindrical member 31 has a distal tip 10a fixed thereto, which may be formed of resin.

In the medical device 5, the second wrapping portion 37 and the second lining portion 38 are fixed to each other at second fixation portions 52, the second fixation portions 52 being within spaces 22b on the circumference of the second cylindrical member 31 that are defined by a first wire 24a and a second wire 26a. Additionally, neither the second wrapping portion 37 nor the second lining portion 38 is fixed to either of the first wire 24a and the second wire 26a that constitute the mesh member 20a (see FIG. 11). As in the case of the cylindrical member 30, the second wrapping portion 37 and the second lining portion 38 of the second cylindrical member 31 may be made of stainless steel and may be fixed to each other within the spaces 22b with an adhesive. However, the method of providing the second fixation portions 52 is not particularly limited.

Because of this configuration, upon radial expansion or radial contraction of the mesh member 20a, movement of the first wire 24a or the second wire 26a is not likely to be interfered with by the cylindrical member 30 or the second cylindrical member 31, and consequently the concentration of stress at either end 21a or 23a of the mesh member 20a is reduced, so that the likelihood of breakage of the first wire 24a or the second wire 26a that constitute the mesh member 20a is further reduced.

In the medical devices 1 to 5 described above, dilation of a stenosis or stricture is achieved by using the mesh member 20 or 20a alone. However, when the stenosis or stricture is calcified and the expansion of the mesh member is not enough, the mesh member may have an incising member (a scoring member) attached on its outer circumference in the longitudinal direction. When attaching the incising member (the scoring member), attention should be paid so that it does not interfere with the movement of the first wire 24 or 24a or the second wire 26 or 26a upon radial expansion or radial contraction of the mesh member 20 or 20a.

In the medical devices 1 to 5 described above, the fixation portions 50, 50a, 50b, 50c, 50d, 52 at which the wrapping portion 32, 32a, or 32b or second wrapping portion 37 and the lining portion 36 or 36a or second wrapping portion 38 are fixed to each other are within all the spaces 22, 22a, or 22b on the circumference of the cylindrical member 30, 30a, or 30b or second cylindrical member 31, the spaces being defined by the first wire 24 or 24a and the second wire 26 or 26a. However, the disclosed embodiments are not limited to this configuration. As long as the first wire 24 or 24a and the second wire 26 or 26a do not move out of position upon radial expansion or radial contraction of the mesh member 20 or 20a, the fixation portions 50, 50a, 50b, 50c, 50d, or 52 may be formed sporadically (in no particular pattern) or in a spiral arrangement on the circumference of the cylindrical member 30, 30a, or 30b, or second cylindrical member 31.

The material of the wrapping portion 32, 32a, or 32b and the lining portion 36 or 36a of the cylindrical member 30, 30a, or 30b is not limited to stainless steel. Preferably, the material thereof is a radiopaque material (tungsten, for example) because, in that case, imaging allows the handler to see exactly where the proximal end 21 or 21a of the mesh member 20 or 20a is and consequently to easily place the mesh member 20 or 20a in a stenosis or stricture. Similarly, the material of the second wrapping portion 37 and the second lining portion 38 of the second cylindrical member 31 is not limited to stainless steel. Preferably, the material thereof is a radiopaque material (tungsten, for example) because, in that case, imaging allows the handler to see exactly where the distal end 23a of the mesh member 20a is and consequently allows the handler to easily place the mesh member 20a in a stenosis or stricture.

The cross-sectional profile of the cylindrical member 30, 30a, or 30b and the second cylindrical member 31 is described above as circular, but the disclosed embodiments are not limited to this configuration. The cross-sectional profile thereof may be elliptical or polygonal, for example.

What is claimed is:

1. A medical device comprising:
   a mesh member capable of radially expanding and radially contracting, the mesh member being woven from a first wire and a second wire and having a proximal end, a distal end opposite to the proximal end, and a middle portion between the proximal end and the distal end;
   a first cylindrical member disposed at the proximal end of the mesh member and not at the middle portion of the mesh member, the first cylindrical member comprising a first wrapping portion and a first lining portion, the first wrapping portion covering an outer circumference of the proximal end of the mesh member, and the first lining portion covering an inner circumference of the proximal end of the mesh member; and
   a shaft fixed to a proximal end portion of the first wrapping portion and extending in a proximal direction away from the distal end of the mesh member, the shaft having a central axis that is radially offset from a central axis of the first cylindrical member,
   wherein:
   the first wrapping portion and the first lining portion are fixed to each other at first fixation portions, the first fixation portions being within spaces that are defined by the first wire and the second wire, and
   neither the first wrapping portion nor the first lining portion is fixed to either of the first wire or the second wire.

2. The medical device according to claim 1, wherein:
   an outer surface of the first wrapping portion has depressed sections and projected sections, the depressed sections being formed at the first fixation portions, and the projected sections being formed where the first wrapping portion and the first lining portion are not fixed to each other, and
   the shaft is fixed to the outer surface of the first wrapping portion at one of the depressed sections.

3. The medical device according to claim 2, further comprising:
   a second cylindrical member disposed at the distal end of the mesh member and not at the middle portion of the mesh member, the second cylindrical member comprising a second wrapping portion and a second lining portion, the second wrapping portion covering an outer circumference of the distal end of the mesh member, and the second lining portion covering an inner circumference of the distal end of the mesh member,
   wherein:
   the second wrapping portion and the second lining portion are fixed to each other at second fixation portions, the second fixation portions being within spaces that are defined by the first wire and the second wire, and neither the second wrapping portion nor the second lining portion is fixed to either of the first wire or the second wire.

4. The medical device according to claim 2, wherein at least one of the first wrapping portion and the first lining portion has a space at one of the depressed sections.

5. The medical device according to claim 4, wherein the first wire and the second wire are capable of moving freely between the first wrapping portion and the first lining portion when the mesh member radially expands or radially contracts.

6. The medical device according to claim 4, wherein a cross-sectional profile of the shaft is elliptical so as to be accommodated between two adjacent projected sections.

7. The medical device according to claim 2, wherein a portion of a cross section of the shaft, taken perpendicular to an axial direction of the first cylindrical member, is accommodated between two adjacent projected sections.

8. The medical device according to claim 2, wherein the first wire and the second wire are capable of moving freely between the first wrapping portion and the first lining portion when the mesh member radially expands or radially contracts.

9. The medical device according to claim 2, wherein a cross-sectional profile of the shaft is elliptical so as to be accommodated between two adjacent projected sections.

10. The medical device according to claim 1, further comprising:
a second cylindrical member disposed at the distal end of the mesh member and not at the middle portion of the mesh member, the second cylindrical member comprising a second wrapping portion and a second lining portion, the second wrapping portion covering an outer circumference of the distal end of the mesh member, and the second lining portion covering an inner circumference of the distal end of the mesh member,
wherein:
the second wrapping portion and the second lining portion are fixed to each other at second fixation portions, the second fixation portions being within spaces that are defined by the first wire and the second wire, and
neither the second wrapping portion nor the second lining portion is fixed to either of the first wire or the second wire.

11. The medical device according to claim 1, wherein at least one of the first wrapping portion and the first lining portion has a space at one of the first fixation portions.

12. The medical device according to claim 11, wherein the first wire and the second wire are capable of moving freely between the first wrapping portion and the first lining portion when the mesh member radially expands or radially contracts.

13. The medical device according to claim 11, wherein a cross-sectional profile of the shaft is elliptical.

14. The medical device according to claim 1, wherein at least one of the first wrapping member and the first lining portion is made of metal.

15. The medical device according to claim 1, wherein the shaft is fixed to an outer surface of the first wrapping portion of the first cylindrical member.

16. The medical device according to claim 1, wherein the first wire and the second wire are capable of moving freely between the first wrapping portion and the first lining portion when the mesh member radially expands or radially contracts.

17. The medical device according to claim 1, wherein a cross-sectional profile of the shaft is elliptical.

18. The medical device according to claim 1, wherein the medical device is configured for dilating a stenosis or stricture.

19. A medical device comprising:
a mesh member capable of radially expanding and radially contracting, the mesh member being woven from a first wire and a second wire and having a proximal end, a distal end opposite to the proximal end, and a middle portion between the proximal end and the distal end;
a first cylindrical member disposed at the proximal end of the mesh member and not at the middle portion of the mesh member, the first cylindrical member comprising a first wrapping portion and a first lining portion, the first wrapping portion covering an outer circumference of the proximal end of the mesh member, and the first lining portion covering an inner circumference of the proximal end of the mesh member; and
a shaft permanently fixed to the first cylindrical member and extending in a proximal direction away from the distal end of the mesh member,
wherein:
the first wrapping portion and the first lining portion are fixed to each other at first fixation portions, the first fixation portions being within spaces that are defined by the first wire and the second wire, and
neither the first wrapping portion nor the first lining portion is fixed to either of the first wire or the second wire.

20. The medical device according to claim 19, wherein the medical device is configured for dilating a stenosis or stricture.

* * * * *